United States Patent [19]
Snyder et al.

[11] 4,056,357
[45] Nov. 1, 1977

[54] DIRECT BILIRUBIN ASSAY

[75] Inventors: Lloyd R. Snyder, Yorktown Heights; Jana Furda, Pleasantville, both of N.Y.

[73] Assignee: Technicon Instruments Corporation, Tarrytown, N.Y.

[21] Appl. No.: 701,186

[22] Filed: June 30, 1976

[51] Int. Cl.$^2$ .......................................... G01N 33/16
[52] U.S. Cl. ................................................. 23/230 B
[58] Field of Search ....................................... 23/230 B

[56] References Cited
PUBLICATIONS

J. Furda et al., Clinical Chemistry, vol. 21, No. 7, 1975, p. 1005.

*Primary Examiner*—Robert M. Reese
*Attorney, Agent, or Firm*—Morgan, Finnegan, Pine, Foley & Lee

[57] ABSTRACT

This invention relates to the use of derivatives of N-1-naphthyl ethylenediamine for standardization of direct bilirubin assays.

2 Claims, No Drawings

DIRECT BILIRUBIN ASSAY

BACKGROUND OF THE INVENTION

This invention relates generally to a novel assay method. More particularly, it relates to an assay method for the detection of direct bilirubin, also called conjugated bilirubin, in serum and other body fluids.

While it is typical in the field of diagnostic analysis to utilize the same compound assayed for as the standard in the clinical determination, e.g. glucose in assays for specimen glucose, it is not a practical solution in the case of direct bilirubin. This material is not only difficult ot obtain but it is relatively unstable.

The prior art has suggested the use of N-1-naphthyl ethylenediamine for the standardization of direct bilirubin assays. It has been found that while N-1-naphthyl ethylenediamine is suitable as a standard for the calibration of direct bilirubin assays in a single-assay system, it is not suitable for clinical analyzers which simultaneously analyze a single specimen for more than one component, particularly where ion-selective electrodes are used in the multi-assay system.

For instance, ion-selective electrodes are used for both sodium and potassium determinations. When N-1-naphthyl ethylenediamine is used for standardizing direct bilirubin in a multi-component system such as in the Technicon SMAC[1] analyzer which requires compatibility with the other nineteen channels of this analyzer, it was found to be unsuitable because values for potassium were falsely elevated when potassium is determined by the normally-used valinomycin ion-selective electrode. As a result, there is a variable interference of N-1-naphthyl ethylenediamine (NEDD) in assays of potassium which varies from 0.1 - 1.5 meg./1 potassium for the desired level of 50 mg NEDD/1.

[1]This is a Registered Trademark of Technicon Instruments Corporation.

A similar interference problem would be found for liquid membrane electrodes as well as in PVC membranes used in the ion-selective electrodes for assays of potassium.

It is therefore one object of this invention to provide a material available for standardization of assays for direct bilirubin in serum, suitable for inclusion in a multi-parameter serum without interference with the simultaneous assay of other components in the specimen, especially potassium.

SUMMARY OF THE INVENTION

Accordingly, this invention relates to a method for assaying direct bilirubin in a multi-assay system which comprises using, as a calbiration standard, a compound having the formulae:

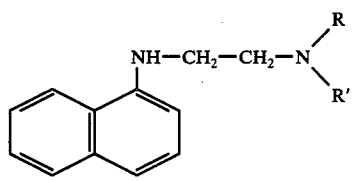

I or

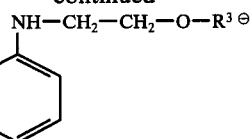

II wherein R is H, akyl containing from 1 to 4 carbon atoms or —$CH_2CH_2$—OH; R' is alkyl from 1 to 4 carbon atoms or —$CH_2CH_2$—OH; and $R^3$ is an anionic moiety.

Particularly preferred compounds for use in the subject method are those having structure I wherein R is H and R' is $CH_3$ (N'-methyl-N-naphthyl-ethylenediamine) and wherein R and R' are both methyl (N',N'-dimethyl-N-naphthyl-ethylenediamine). For both these compounds, solubilization for use in the analyzer may be enhanced by conversion to the corresponding addition salt, e.g. by treatment with $CH_3I$ to form quaternary ammonium salt.

Still others of preference are those having structure I wherein R is H and R' is $CH_2CH_2OH$ (N-naphthyl, N'-monohydroxyethyl ethylenediamine) and wherein R and R' are both $CH_2CH_2OH$ (N-naphthyl, N',N'-dihydroxyethyl ethylenediamine).

Yet another preferred compound for use in the subject method has structure II wherein $R^3$ is $OPO_3H^-$ or $SO_3^-$.

DETAILED DESCRIPTION OF THE INVENTION

The compounds described for use in the diagnostic-method herein disclosed can be prepared according to various synthetic procedures known in the art. Some are commerically available.

On a synthesis basis, one can alkylate N-1-naphthyl ethylenediamine to obtain the compounds having structure I whereas alkylation of naphthylamine with the appropriate alkylating agent will provide the compounds embraced by structure II.

Besides freedom from interference on potassium and other assays, a calibration standard for direct bilirubin must possess other properties. It must be capable of undergoing a color reaction in the direct bilirubin assay that parallels that of direct bilirubin in terms of reaction rate, sensitivity, wavelength of maximum absorption, etc. It must also be adequately soluble in the reconstituted standard and in the reaction mixture used for the assay.

The direct bilirubin method, in a multi-assay system includes the use of two independent but interelated channels: a sample channel and a blank channel. In the sample channel the serum sample is added to a stream of direct bilirubin diluent containing the calibration standard. The stream reacts with a diazo reagent, e.g. the reaction product of sulfanilic acid and sodium nitrite to form an azobilirubin complex.

Since the direct reaction is time dependent, the reaction is stopped after 1 minute by the addition of ascorbic acid which inactivates the diazo reagent. Upon the addition of an alkaline buffer to the serum sample, a conversion in color takes place from the netural pink to the alkaline blue azobilirubin.

In the blank channel, the sample is added to the direct bilirubin diluent followed by a similar chemical environment as in the sample channel above except for addition of sodium nitrite; therefore, no diazo reagent forms. As a result, the absorbance determined in the blank channel is produced predominately by endogenous serum pigments.

As the sample and blank analytical streams reach the colorimeter flowcells, the absorbance of each stream is measured at 550 nm. Blank subtraction is accomplished automatically.

Since there are 19 other channels on an analyzer of the type just described, the calibration standard must be compatible with the chemistries which take place in those other channels. When the compounds disclosed herein are used in the analyzer system described above, the interference problem discussed earlier is eliminated.

This will be apparent from the results contained in the examples provided hereinbelow.

EXAMPLE I

A. Materials and Procedures

Analytical determinations were performed on a SMAC[1] analyzer and an AutoAnalyzer[1] II continuous-flow analyzer, both involve multi-assay systems. Reagents were the usual reagents as described earler. The method of Jendrassik and Grof (Biochem 2 297:81-89 (1938) Ger.) as modified by Gambino (Automation Analytical Chemistry, Technicon Symposia, 1964) was followed. A model 2400-2 spectrophotometer (Gilford Instrument Labs) was used to determine absorption spectra.

[1]These are Registered Trademarks of Technicon Instruments Corporation.

B. Analytical Cartridge

The sample is mixed with HCl (10 mmol/liter), and passes through a five-turn mixing coil, after which the diazo agent is added. The volume of the second coil is selected to give a total coupling time of 1 min. (The addition of ascorbic acid stops the reaction, and finally alkaline tartrate is added to shift the azobilirubin chromogen to the alkaline range. ) Blank determinations are performed simultaneously by using an identical duplicate flow path on the same cartridge, substituting sulfanilic acid for the diazo reagent. Absorbances of assay and blank are measured at 550 nm.

C. Procedures

Pooled serum containing a high concentration of direct-reacting bilirubin was prepared by freezing human serum specimens containing above-normal concentrations of direct-reacting bilirubin. These tubes were stored at −20° C and their contents were thawed immediately before use. The concentration of direct-reacting bilirubin in the pool was established by multiple assays according to the manual method recommended by Gambino (Standard Methods of Clinical Chemisty, Academic Press, Inc., New York, N.Y. 1968, p. 58) as modified from the method of Nosslin (Scand. J. Clin. Lab. Invest. 12, Suppl. 49, 1 (1960).

N'-Methyl-N-1-naphthyl ethylenediamine dihydrochloride (MMN), 50 mg/liter was added to the calibration serum before lyophilization. When reconstituted with diluent, this concentration of MMN should give a direct-reacting value corresponding to about 19 mg/liter for bilirubin by the SMAC method; the exact value is established by assaying the SMAC calibration serum against the pool of human serum (described above) containing a known concentration of direct-reacting bilirubin. The value obtained for the SMAC calibration serum containing MMN is used subsequently in the usual manner for all direct-bilirubin calibrations. A human pooled serum of known direct-bilirubin concentration can be used as a control.

The absorption maxima was determined for coupled MMN, NEDD and the direct-bilirubin fraction. Each specimen was run manually by adding the reagents in the same proportion and under the same conditions as in the automated procedure. The absorption spectra of these compounds were determined over the range of 400 to 700 nm.

The time course of this reaction was studied for MMN, NEDD, and the direct-reacting bilirubin in human serum. As in the previously described procedure, serum was manually added to 10 mmol/liter HCl followed by the diazo reagent. Coupling time was measured by varying the reaction time between 0 and 5 min., at 1-min. intervals. Ascorbic acid was then added, to stop the reaction, followed by the alkaline tartrate reagent. The resulting absorbance was measured in a Gilford Model 2400-2 spectrophotometer.

The effect on the other determinations of incorporating MMN into The SMAC calibration serum was investigated. A SMAC analyzer was calibrated by using Technicon$^{TM}$ SMAC$^{TM}$ I calibration serum. Eight samples of SMAC I calibration serum with MMN and eight samples of control sera were run against this standardization. The system was recalibrated with SMAC I calibration serum containing MMN and eight samples each of regular SMAC I calibration serum, and the frozen controls were run vs. this new calibration.

the analytical linearity of the SMAC I calibrant with MMN was investigated for the direct-bilirubin method. A stock (1 g/liter) solution of MMN was prepared and 27.3 ml of this solution was diluted to 100 ml with SMAC I diluent (equivalent to 100 mg of bilirubin per liter), and 20 ml of this solution was then used to reconstitute normal SMAC I calibration serum. SMAC I calibration serum was then diluted to give concentrations of MMN equivalent to 20, 40, 60, 80, and 100 mg of direct bilirubin per liter.

Values were then correlated for direct-reacting bilirubin obtained on the same specimens assayed on the SMAC and the AutoAnalyzer II by the Jendrassik-Grof procedure.

D. Results and Discussion

At a concentration of 38 mg/1, the NEDD interferred with the potassium assay, causing an increase in value of 0.25 - 2.0 mmol/liter, while the effect with MMN was 0.2 as great, the interference depending upon the particular membrane used.

EXAMPLE II

Instead of MMN, the following calibration standards are used following the procedure of Example I with similar results:

N',N'-dimethyl-N-naphthyl ethylenediamine hydrochloride

N-naphthyl, N'-monohydroxyethyl ethylenediamine

N-naphthyl, N',N'-dihydroxyethyl ethylenediamine

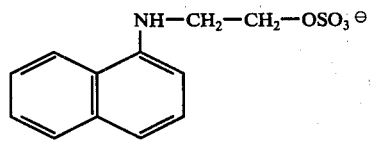

It should be understood by those skilled in the art that various modifications may be made in the present invention without departing from the spirit and scope thereof as described in the specification and defined in the appended claims.

What is claimed is:

1. In a method for assaying direct bilirubin in a multi-assay system, the improvement which comprises using, as a calibration standard, the compound

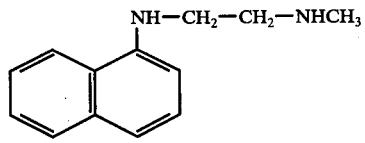

or addition salts thereof.

2. The method of claim 1 wherein said compound is N'-methyl-N-1-naphthyl ethylenediamine dihydrochloride.

* * * * *